US009078805B2

(12) United States Patent
Mueller

(10) Patent No.: US 9,078,805 B2
(45) Date of Patent: Jul. 14, 2015

(54) METHOD FOR PRODUCING A DRUG DELIVERY SYSTEM ON THE BASIS OF POLYELECTROLYTE COMPLEXES

(75) Inventor: Martin Mueller, Dresden (DE)

(73) Assignee: LEIBNIZ-INSTITUT FUER POLYMER-FORSCHUNG DRESDEN E.V., Dresden (DE)

( * ) Notice: Subject to any disclaimer, the term of this patent is extended or adjusted under 35 U.S.C. 154(b) by 5 days.

(21) Appl. No.: 13/638,413

(22) PCT Filed: Mar. 30, 2011

(86) PCT No.: PCT/EP2011/054905
§ 371 (c)(1),
(2), (4) Date: Dec. 12, 2012

(87) PCT Pub. No.: WO2011/121019
PCT Pub. Date: Oct. 6, 2011

(65) Prior Publication Data
US 2013/0108774 A1 May 2, 2013

(30) Foreign Application Priority Data
Apr. 1, 2010 (DE) .......................... 10 2010 003 615

(51) Int. Cl.
| B05D 3/04 | (2006.01) |
| A61F 2/00 | (2006.01) |
| A61J 3/00 | (2006.01) |
| A61L 31/16 | (2006.01) |
| A61K 9/00 | (2006.01) |
| A61K 9/51 | (2006.01) |
| A61L 17/00 | (2006.01) |
| A61L 27/34 | (2006.01) |
| A61L 27/54 | (2006.01) |

(52) U.S. Cl.
CPC ................. *A61J 3/00* (2013.01); *A61K 9/0024* (2013.01); *A61K 9/5146* (2013.01); *A61K 9/5161* (2013.01); *A61L 17/005* (2013.01); *A61L 27/34* (2013.01); *A61L 27/54* (2013.01); *A61L 31/16* (2013.01); *B05D 3/0493* (2013.01); *A61L 2300/432* (2013.01); *A61L 2300/608* (2013.01)

(58) Field of Classification Search
CPC .............................. B05D 3/0493; A61L 31/16
USPC ..................... 427/350, 2.1; 424/423
See application file for complete search history.

(56) References Cited

U.S. PATENT DOCUMENTS

| 2002/0198315 | A1 | 12/2002 | Hutchinson | |
| 2003/0236514 | A1* | 12/2003 | Schwarz ..................... | 604/890.1 |
| 2005/0037050 | A1 | 2/2005 | Weber | |
| 2005/0158359 | A1* | 7/2005 | Epstein et al. ................. | 424/423 |
| 2007/0067882 | A1* | 3/2007 | Atanasoska et al. .......... | 977/904 |
| 2007/0110785 | A1* | 5/2007 | Tedeschi ....................... | 424/423 |
| 2007/0110804 | A1* | 5/2007 | Royer ........................... | 424/468 |
| 2009/0186069 | A1* | 7/2009 | DeYoung et al. ............. | 424/426 |

FOREIGN PATENT DOCUMENTS

| EP | 0 551 626 | 7/1993 |
| EP | 1 575 633 | 9/2005 |
| WO | 99/15150 | 4/1999 |
| WO | 2004/112713 | 12/2004 |
| WO | 2008/033497 | 3/2008 |

OTHER PUBLICATIONS

Rajendran et al. Alginate-Chitosan Particulate System for Sustained Release of Nimodipine. Trop J Pharm Res, Oct. 2009; 8 (5): 4 33.*
Liao e tal. Controlled release from fibers of polyelectrolyte complexes. Journal of Controlled Release 104 (2005) 347-358.*
Huang et al. Polyelectrolyte Complexes Stabilize and Controllably Release Vascular Endotheial Growth Factor. Biomacromolecules. vol. 8. 2007.1607-1614.*
P.B. Malafaya et al., "Drug Delivery Therapies I General trends and its Importance on Bone Tissue Engineering Applications," Current Opinion in Solid State and Materials Science, vol. 6 (2002) pp. 283-295.
P.B. Malafaya et al., "Drug delivery therapies II. Strategies for delivering bone regenerating factors," Current Opinion in Solid State and Materials Science, vol. 6 (2002) pp. 297-312.
Burkart Philipp et al., "Polyelectrolyte Complexes—Recent Developments and Open Problems," Prog. Polym. Sci., vol. 14, 1989, pp. 91-172.
D.D.Lasic et al., "Medical Applications of Liposomes," Elsevier Science B.V., 1998, pp. 1-2.
Sukhorukov et al., "Nanoengineered Polymer Capsules: Tools for Detection, Controlled Delivery, and Site-Specific Manipulation," Small, vol. 1, No. 2 (2005) pp. 194-200.
Coppi et al., "Alginate/chitosan microparticles for tamoxifen delivery to the lymphatic system," International Journal of Pharmaceutics, vol. 367 (2009) pp. 127-132.
Helmut Ringsdorf, "Structure and Properties of Pharmacologically Active Polymers," Polymer: Symposium No. 51, (1975) pp. 135-153.
Harjit Tamber et al., "Formulation Aspects of Biodegradable Polymeric Microspheres for Antigen Delivery," Advance Drug Delivery Reviews, vol. 57 (2005) pp. 357-376.

(Continued)

*Primary Examiner* — Cachet Sellman
(74) *Attorney, Agent, or Firm* — Greenblum & Bernstein, P.L.C.

(57) ABSTRACT

A method that relates to the fields of polymer chemistry, pharmacy and medicine and releases drugs as a component of implants into the environment of the implant. A method that, in a simple and easily reproducible manner, generates a drug delivery system, which releases drugs in a locally targeted and controllably delayed manner. Polyanions and polycations are mixed in a liquid in a non-stoichiometric ratio, relative to the charged monomer units, wherein drugs are added to the polyelectrolytes either before, during or after the mixing, or charge-carrying drugs and an oppositely charged polyelectrolyte are mixed, and after the mixing the polyelectrolyte complex produced is applied to the surface of a medical structure or material or is positioned on the surface directly at the location where the drug is to be released.

32 Claims, No Drawings

(56) References Cited

OTHER PUBLICATIONS

Xianhua Feng et al., "Adhesion of Colloidal Polyelectrolyte Complexes to Wet Cellulose," Biomacromolecules, vol. 8, Jun. 15, 2007, pp. 2161-2166.

Min Huang et al., "Polyelectrolyte Complexes Stabilize and Controllably Release Vascular Endothelial Growth Factor," Biomacromolecules, vol. 8 (2007) pp. 1607-1614.

P. Dubin et al., "Macromolecular Complexes in Chemistry and Biology," (1994) pp. 1-3.

Paloma M. de la Torre et al., "Release of amoxicillin from polyionic complexes of chitosan and poly(acrylic acid). Study of polymer/polymer and polymer/drug interactions within the network structure," Biomaterials, vol. 24 (2003) pp. 1499-1506.

Pimwipha Piyakulawat et al., "Preparation and Evaluation of Chitosan/Carrageenan Beads for Controlled Release of Sodium Diclofenac," AAPS PharmSciTech, vol. 8, No. 4 Article 97, Nov. 16, 2007, pp. E1-E-11.

Junjie Li et al., "Formation of Nano-hydroxyapatite crystal in situ in chitosan-pectin polyelectrolyte complex network," Materials Science and Engineering C, vol. 30 (2010) pp. 795-803 (available online: Mar. 31, 2010).

Karen Kohler et al., "Drastic Morphological Modification of Polyelectrolyte Microcapsules Induced by High Temperature," Macromolecules, vol. 37, (2004) pp. 9546-9550.

Li-Ying Huang et al., "Surface immobilization of chondroitin 6-sulfate/heparin multilayer on stainless steel for developing drug-eluting coronary stents," Colloids and Surfaces B: Biointerfaces, vol. 61 (2008) pp. 43-52.

Markus Antonietti et al., "Vesicles and Liposomes: A Self-Assembly Principle Beyond Lipids," Advanced Materials, vol. 15, No. 16, Aug. 15, 2003, pp. 1323-1333.

Ouyang, W. et al., "Monomodal polyelectrolyte complex nanoparticles of PDADMAC/Poly(sturenesulfonate): Preparation and protein interaction," Macromol. Biosci. 2006, 6, 929-941.

Tiyaboonchai, W. et al., "Formulation and characterization of amphotericin B-chitosan-dextran sulfate nanoparticles," Int. Journal of Pharamceutics 329 (2007), 142-149, Aug. 17, 2006.

Tiyaboonchai, W. et al., "Formulation and characterization of amphotericin B-chitosan-dextran sulfate nanoparticles," Journal of Pharamceutical Sciences, vol. 90, No. 7 , Jul. 2001, 902-914.

Tiyaboonchai, W. et al., "Formulation and characterization of DNA-polyethylenimine-dextran sulfate nanoparticles", European Journal of Pharmaceutical Sciences 19 (2003) pp. 191-202.

Petrov, Alexander et al., "Protein-Calcium Carbonate Coprecipitation: A Tool for Protein Encapsulation," Biotechnol. Prog. (2005) 21, pp. 918-925, Apr. 26, 2005.

Tiwari, Ananya et al., "Kinetics of Protein-Protein Complex Coacervation and Biphasic Release of Salbutamol Sulfate from Coacervate Matrix," Biomacromolecules 2009, 10, pp. 184-185.

Kim, Taek Gyoung et al., "Controlled gene-eluting metal stent fabricated by bio-inspired surface modification with hyaluronic acid and deposition of DNA/PEI polyplexes," Int. Journal of Pharamceutics 384 (2010), 181-188, available online: Sep. 30, 2009.

Kabanov, V.A. et al., "Soluble interpolymeric complexes as a new classic of synthetic polyelectrolytes," Pure & Appl. Chem., vol. 56, No. 3, pp. 343-354 (1984).

Search report from International Application No. PCT/EP2011/054905, mail date is May 7, 2012.

\* cited by examiner

METHOD FOR PRODUCING A DRUG DELIVERY SYSTEM ON THE BASIS OF POLYELECTROLYTE COMPLEXES

CROSS-REFERENCE TO RELATED APPLICATIONS

The present application is a U.S. National Stage Application of International Application No. PCT/EP2011/054905 filed Mar. 30, 2011, which published as WO 2011/121019 A2 on Oct. 6, 2011, the disclosure of which is expressly incorporated by reference herein in its entirety. Further, the present application claims priority under 35 U.S.C. §119 and §365 of German Application No. DE 10 2010 003 615.3, filed Apr. 1, 2010.

BACKGROUND OF THE INVENTION

1. Field of the Invention

The invention relates to the fields of polymer chemistry, pharmacy and medicine and relates to a method for producing a drug delivery system on the basis of polyelectrolyte complexes, which, for example, as a component of implants, releases drugs in the environment of the implant.

2. Discussion of Background Information

For the provision of release or so-called drug delivery systems (DDS) with the release of drugs (AS) at biomedically relevant positions on the one hand a great need exists as well as a great need for action. DDS have been continuously researched from the beginnings around 1940 through the present day. They are an important component in the transfer of new drugs into clinical practice. [B. Malafaya, et al. (2002): Curr. Opinion Solid State Mater. Sci. 6, 283-312 (Part I), 297-312. (Part II)]

New active agent-loaded polymer systems [H. Tamba, et al. (2005). Adv. Drug Deliv. Rev. 57, 357-376; G. B. Sukohorukov, et al. (2005). Small, 182, 194-200.] seem particularly promising for this purpose. In this context on the one hand classic systems of surfactant or (co)polymer liposomes [H. Ringsdorf (1975). Polym. Sci. Polymer Symp. 51, 135-153; D. D. Lasic (1998) Medical applications of Liposomes, Papahadjopoulos D., Ed.; Elsevier; M. Antonietti, S. Förster (2003). Advanced Materials 15, 1323-1333.] can be used. On the other hand, polyelectrolyte hollow capsules [A. I. Petrov, et al. (2005). Biotechnol. Prog. 21, 918-925; K. Köhler, et al. (2004) Macromolecules 37, 9546-9550] render possible the physical inclusion of active ingredients.

Polyelectrolyte complexes (PEC) are generally known. They are produced by complexing oppositely charged polyelectrolytes (PEL). With this complexing, the PEC can be formed in the form of dispersed spherical-like PEC nanoparticles. These PEC nanoparticles are obtained by the controlled mixing of polycation solutions and polyanion solutions in non-stoichiometric molar ratios, [V. A. Kabanov, et al (1984). Pure Appl. Chem, 56, 343-354; B. Philipp, et al. (1989). Prog. Polym. Sci. 14, 91-172]. PEC nanoparticles are composed of a rather hydrophobic charge-compensated core and a hydrophilic shell, which is formed by the respective excess PEL (polycation or polyanion). PEC nanoparticles are interesting among other things for the surface modification of technical substrates, [X. Feng, et al. (2007) Biomacromolecules 8, 2161-2166]. Already preformed nanoparticles can thereby preferentially be bound to the corresponding substrate or the complexing step takes place in the presence of the substrate.

A great potential of the PEC particles is seen for nano carrier systems in the volume phase in the field of biomedicine and pharmacy [P. Dubin, et al. (eds.) (1994) Macromolecular Complexes in Chemistry and Biology, Springer-Verlag].

In this context, studies by Tiyaboonchai [W. Tiyaboonchai et al. (2001) J. Pharm. Sci. 90, 902-914] are known, in which the formulation and characterization of nanoparticles of poly (ethylenimine) (PEI), dextran sulfate (DS) and amphotericin B (AmB) is described. AmB is an antifungal drug for systemic fungal infections, but due to the low water solubility is not absorbed by the gastrointestinal tract. Likewise, the development of a breast cancer therapeutic agent on the basis of chitosan-alginate microparticles has been studied [G. Coppi, et al. (2009), Int. J. Pharmaceut. 367, 127-132], in which the absorption and time-dependent release of Tamoxifen was tested.

Furthermore, the absorption of Salbutamol, a therapeutic agent for asthma, on complex particles from the two oppositely charged proteins gelatin A and gelatin B in the submicrometer range and the delayed release thereof in gastrosimulating liquids is described [A. Tiwari, et al. (2009). Biomacromolecules 10, 184-189]. Salbutamol was added during and after the complexing. As an important propelling power of the release, the osmotic pressure difference between the particle interior and the environment was cited. Also interesting with respect to the invention, are studies on the use of PEC particles as carrier systems in general for proteins [W. Ouyang, et al. (2006). Macromol. Biosci. 6, 929-941], specifically for growth factors (VEGF) (chitosan/dextran sulfate) [M. Huang, et al. (2007) Biomacromolecules 8, 1607-1614], but also for plasmid DNA [W. Tiyaboonchai, et al. (2003) Eur. J. Pharm. Sci. 19, 191-202].

There are disadvantages in the known technical solutions for drug delivery systems above all in the still not yet adequate accuracy with locally controlled releases of drugs at the desired sites as well as in the speed and quantity of the release of the drug.

SUMMARY OF EMBODIMENTS OF THE INVENTION

An aim of the present invention is to disclose a method for the production of a drug delivery system on the basis of polyelectrolyte complexes, which in a simple and easily reproducible manner, generates a drug delivery system which releases drugs in a locally targeted and controllably delayed manner.

The aim is attained by the invention disclosed in the claims. Advantageous embodiments are the subject matter of the subordinate claims.

Aspects of embodiments of the present invention are directed to a method for producing a drug delivery system on the basis of polyelectrolyte complexes. The method comprises producing a polyelectrolyte complex. The producing comprises mixing a polyelectrolyte solution comprising polyanions and a polyelectrolyte solution comprising polycations relative to charged monomer units in a liquid in a non-stoichiometric ratio, wherein at least one drug is added to at least one of the polyelectrolyte solutions one of before, during and after the mixing, or at least one charge-carrying drug and an oppositely charged polyelectrolyte are mixed. The method further comprises applying a layer of the polyelectrolyte complex produced to a surface or a surface region of a medical structure or material, or positioning the polyelectrolyte complex produced on the surface or the surface region directly at a location where the at least one drug is to be released.

In embodiments of the present invention, the polyanions comprise at least one of anionic polypeptides, poly(L-glutamic acid), poly(D-glutamic acid), anionic polysaccharides, dextran sulfate, heparin, cellulose sulfate, carboxymethyl cellulose, carboxymethyl starch, alginate, carrageenan, xanthan, hyaluronic acid, and poly(acrylic acid).

In further embodiments of the present invention, the polycations comprise at least one of cationic polypeptides, poly(L-lysine), poly(D-lysine), cationic polysaccharides, diethylaminoethyl (DEAE) dextran, chitosan, cationic starch, poly(methylene-co-guanidine), and poly(ethyleneimine).

In additional embodiments of the present invention, the liquid comprises water with adjusted pH value, ionic strength and temperature.

In yet further embodiments of the present invention, the polyanions and the polycations are mixed in a value coming as close as possible to the stoichiometric ratio of 1, relative to the charged monomer units.

In embodiments of the present invention, the polyanions and the polycations are mixed in a non-stoichiometric ratio of (0.5 to <1) to (>1 to 2).

In further embodiments of the present invention, the polyanions and the polycations are mixed in a non-stoichiometric ratio of (0.9 to <1) to (>1 to 1.1).

In additional embodiments of the present invention, the non-stoichiometric ratio of the polycations and polyanions is realized via utilizing different volumes with a same concentration of the polycations and the polyanions relative to the charged monomer units.

In yet further embodiments of the present invention, the method further comprises adding a charge-carrying drug to one of the polyelectrolyte solutions for the production of a drug-PEC dispersion.

In embodiments of the present invention, the at least one drug is added in a quantity corresponding to a stoichiometric ratio to the charged monomer units of the oppositely charged polyelectrolyte of less than 1.

In further embodiments of the present invention, the at least one drug comprises a drug carrying single or multiple anionic and/or cationic charges, or charge-carrying antibiotics.

In additional embodiments of the present invention, the at least one drug comprises bisphosphonates (BP).

In yet further embodiments of the present invention, the at least one drug comprises at least one of streptomycin, gentamicin, penicillin and nystatin.

In embodiments of the present invention, the at least one drug comprises at least one uncharged drug.

In further embodiments of the present invention, the at least one drug comprises at least one of proton-pump inhibitors (PPI), statins (STA), and proteasome inhibitors (PSI) are used.

In additional embodiments of the present invention, the proton-pump inhibitors (PPI) comprise pantoprazole.

In yet further embodiments of the present invention, the statins comprise pravastatin.

In embodiments of the present invention, the proteasome inhibitors (PSI) comprise bortezomib.

In further embodiments of the present invention, the at least one drug comprises a plurality of drugs, wherein the plurality of drugs are released in one of an identically and differently delayed manner.

In additional embodiments of the present invention, the mixing of the polyelectrolytes comprises preparative process parameters.

In yet further embodiments of the present invention, the process parameters comprise at least one of order of addition, stirring rate, and consecutive steps of centrifuging-decanting-redispersing.

In embodiments of the present invention, with the production of the non-stoichiometric mixtures of polyanion/polycation and of polyelectrolyte/drug, relative to the charged monomer units of the polyelectrolytes and the charged groups of the drug, a respective excess (majority) component is presented, the method further comprising adding a respective deficit (minority) component.

In further embodiments of the present invention, the producing the polyelectrolyte complex comprises producing a PEC dispersion, comprised chiefly of monomodally distributed nanoscale particles (polyelectrolyte complex particles—PEC particles).

In additional embodiments of the present invention, the producing the polyelectrolyte complex comprises producing PEC dispersions of polymodally distributed nanoscale particles with particle diameters in the range of 10 to 1000 nm.

In yet further embodiments of the present invention, the producing the polyelectrolyte complex comprises producing a PEC dispersion of PEC particles having at least one of soft and latex properties.

In embodiments of the present invention, the applying the polyelectrolyte complex to the surface of the medical structure or material comprises one of adsorption, immersion, spraying, brushing, flowing over/streaming over, and the method further comprises drying the applied polyelectrolyte complex layer by raising the temperature, such that a solvent is removed, whereby a stable or irreversibly surface-bonded layer is produced.

In further embodiments of the present invention, the method further comprises rinsing the applied polyelectrolyte complex layer with water after the applying the polyelectrolyte complex layer.

In additional embodiments of the present invention, a liquid component of the applied polyelectrolyte complex layer is removed by lowering the pressure (vacuum).

In yet further embodiments of the present invention, the medical structure or material comprises at least one of implants, bone-replacement materials, wound closures, and suture materials.

In embodiments of the present invention, the positioning of the polyelectrolyte complex comprises a local injection.

In further embodiments of the present invention, the method further comprises adding at least one of inorganic salts and buffer substances to one of the two polyelectrolyte solutions, to both polyelectrolyte solutions, to the drug solution, to the polyelectrolyte/drug mixture, or to the PEC dispersion obtained by mixing.

In additional embodiments of the present invention, the inorganic salt comprises calcium chloride.

In yet further embodiments of the present invention, the buffer substances comprises a citrate buffer.

With the method according to the invention for the production of a drug delivery system on the basis of polyelectrolyte complexes, polyanions and polycations in a non-stoichiometric ratio, relative to the charged monomer units are mixed in a liquid, wherein one, two or more drugs are added either before, during or after the mixing to the polyelectrolytes, or one, two or more charge-carrying drugs and an oppositely charged polyelectrolyte are mixed, and after the mixing the polyelectrolyte complex produced is applied to the surface or the surface region of a medical structure or material or is positioned on the surface or the surface region directly at the location where the drug is to be released.

Advantageously, anionic polypeptides, poly(L-glutamic acid), poly(D-glutamic acid), anionic polysaccharides, dextran sulfate, heparin, cellulose sulfate, carboxymethyl cellulose, carboxymethyl starch, alginate, carrageenan, xanthene, hyaluronic acid, poly(acrylic acid) are used as polyanions.

Likewise advantageously cationic polypeptides, poly-L-lysine, poly-D-lysine, cationic polysaccharides, diethylaminoethyl (DEAE) dextran, chitosan, cationic starch, poly(methylene-co-guanidine), poly(ethyleneimine) are used as polycations.

Furthermore advantageously, water with adjusted pH value, ionic strength and temperature is used as liquid.

And also advantageously, polyanions and polycations are mixed in a value coming as close as possible to the stoichiometric ratio of 1, relative to the charge-carrying monomer units.

It is likewise advantageous if polyanions and polycations are mixed in a non-stoichiometric ratio of (0.5 to <1) to (>1 to 2), advantageously (0.9 to <1) to (>1 to 1.1).

And it is also advantageous if the non-stoichiometric ratio of the polycations and polyanions is realized via different volumes with the same concentration of the polycations and polyanions relative to the charge-carrying monomer units.

It is furthermore advantageous if a drug is added before the mixing of a polyelectrolyte solution, during the mixing or after the mixing of the polyelectrolyte solutions.

It is likewise advantageous if for the production of a drug-PEC dispersion a charge-carrying drug is added to one of the polyelectrolyte solutions.

Furthermore it is advantageous if the drug is added in a quantity that corresponds to a stoichiometric ratio to the charged monomer units of an oppositely charged polyelectrolyte of less than 1.

And it is also advantageous if drugs carrying single or multiple anionic and/or cationic charges, advantageously bisphosphonates (BP), or charge-carrying antibiotics, advantageously streptomycin, gentamicin, penicillin and/or nystatin are used.

It is also advantageous if uncharged drugs are used.

It is furthermore advantageous if proton-pump inhibitors (PPI) such as pantoprazole and/or statins (STA), such as pravastatin, and/or proteasome inhibitors (PSI) such as bortezomib are used as drugs.

It is likewise advantageous if two and more drugs are used and they are released in an identically or differently delayed manner.

It is also advantageous if the mixing of the polyelectrolytes is realized by preparative process parameters, such as order of addition, stirring rate, consecutive steps of centrifuging-decanting-redispersing.

It is also advantageous if with the production of the non-stoichiometric mixtures of polyanion/polycation and of polyelectrolyte/drug, relative to the charged monomer units of the polyelectrolytes and the charged groups of the drug, the excess component is presented and the deficit component is added.

And it is also advantageous if a PEC dispersion is produced, which is composed chiefly of monomodally distributed nanoscale particles (polyelectrolyte complex particles—PEC particles) with defined particle size and defined charge sign.

It is furthermore advantageous if PEC dispersions of polymodally distributed nanoscale particles with particle diameters in the range of 10 to 1000 nm are used.

And it is likewise advantageous if PEC dispersions are produced, the PEC particles of which have latex-like properties.

Advantageously, the polyelectrolyte complex is applied to the surface of medical structures or materials by adsorption, immersion, spraying, brushing, flowing over/streaming over, and the applied layer is dried by raising the temperature and the solvent is removed, whereby a stable or irreversibly surface-bonded layer is produced.

Furthermore advantageously, after the application of the polyelectrolyte complex the applied layer is rinsed with water.

And it is also advantageous if the liquid component of the applied layer is removed by lowering the pressure (vacuum).

It is also advantageous if implants, bone-replacement materials, wound closures, suture materials are used as medical structures or materials.

And also advantageously the direct positioning of the polyelectrolyte complex is realized by local injection.

It is likewise advantageous if inorganic salts, such as calcium chloride, and/or buffer substances, such as citrate buffer, are added to one of the two or both polyelectrolyte solutions or to the drug solution or to the polyelectrolyte/drug mixture or the PEC dispersion obtained by mixing.

DETAILED DESCRIPTION OF EMBODIMENTS OF THE INVENTION

With the solution according to the invention it is possible for the first time to release drugs in a locally targeted and controllably delayed manner by the use of polyelectrolyte complexes.

According to the invention, polycations and polyanions are mixed in a non-stoichiometric ratio and the drug is added advantageously during mixing. The concentration, the pH value, the ionic strength and the molar ratio of the polyelectrolytes and the drug must thereby be coordinated with one another so that a defined stoichiometric ratio relative to the monomer units of the two polyelectrolytes is adjusted. During the mixing of the polycations and polyanions in a liquid in an advantageously slightly non-stoichiometric ratio, an at least weakly charged polyelectrolyte complex (PEC) is produced. The net charge of the polyelectrolyte complex is determined by the excess component so that the polyanion or anionic monomer units in excess leads to negatively charged PEC particles and the polycation or cationic monomer units in excess lead to positively charged PEC particles. Advantageously the polyelectrolyte solution with the excess charged monomer units (excess polyelectrolyte) is presented and the polyelectrolyte solution with the minor amounts of oppositely charged monomer units (deficit polyelectrolyte) is added.

Depending on which charge the drugs used have, the polyelectrolyte complex produced is advantageously structured such that it is at least weakly charged oppositely to the drug. In the event that the drug bears cationic or anionic charges, the drug is then already a constituent of the complex.

Advantageously the polyelectrolyte complex produced should have at least one weak opposite charge to the drug, so that the drug can be kept longer in the complex.

Polyelectrolyte complexes are generally present as aqueous dispersions, which are composed essentially of nanoscale particles (polyelectrolyte complex particles—PEC particles), the optionally positive or negative net charge of which can be adjusted by the mixing ratio. PEC particles have a soft, latex-like structure with a charge-compensated hydrophobic core and a charged hydrophilic shell (core/shell particle), and are detectable by methods such as dynamic light scattering or in-situ ATR-FTIR spectroscopy in a special flow cell (M. Müller et al. Langmuir 2005, 21, 7044-7051). The particle diameter thereof can be adjusted by structure and media parameters in the range of 10-1000 nm and under standard conditions is generally 150-300 nm. Freshly produced PEC particle dispersion as a rule have size distributions of differing widths, which optionally can be narrowed considerably by consecutive steps of centrifuging, separation and redispersion.

During the production of drug-loaded PEC particles, the drug is incorporated into the particle core as well as attached into the particle shell.

According to the invention, the drug-loaded PEC particles are applied to biomedically relevant surfaces of the medical structure or material. The deposition can be carried out by immersion and adsorption, flowing over, brushing on or spraying on, in each case followed by a drying step.

The PEC particles thereby after the application onto the surface of the medical structure or material and removal of the liquid form a latex-like layer, which is composed of the still relatively soft or partially fused PEC particles with the drug. If the medical structure or material has charged functional groups on the surface, advantageously the oppositely charged PEC particles are applied.

After the introduction of a medical structure or material thus modified at the desired location and environment, for example of an implant in a tissue, the drug is released. The drug located on the shell of the PEC particle is thereby first released in the milieu of the environment (among other things, extracellular tissue fluid, blood) of the medical structure or material. Subsequently, the drug located further in the interior of the PEC particle is released in a delayed manner. During the release diffusive and osmotic processes play a role.

The controllably delayed release of the drug from the PEC is achieved according to the invention in that the drugs are located partially in the PEC particle core and partially on the particle shell.

Aqueous solutions, after expedient adjustment and selection of salt concentration, buffer substance type and pH value, are advantageously used as release media.

The PEC particle/drug layers produced after the application to the surface of the medical structure or material are stable against solution in water and various buffer solutions. They therefore do not represent a negative influence for the surrounding tissue and for example can later also be removed again with the medical structure or material.

The mode of operation of a deposited drug-loaded PEC dispersion of this type results from the comparison to the deposited pure active substance: for the drug bound in and on the PEC particle, compared to the pure drug layer, delayed release kinetics result in contact with the aqueous release medium.

It is particularly advantageous in the deposition on medical structures or materials that the deposited layers of PEC particle/drug essentially firmly adhere to the surface and are irreversibly deposited.

In the case of medical implant-supported regenerative operations, the PEC particle/drug dispersions are applied directly onto the implant by immersion, spraying or brushing on with subsequent drying. A proportion of the drug and the residue can thereby be initially already adjustably released postoperatively in a delayed manner.

The release of the drug can be adjusted individually to the biomedical application by varying the cationic and anionic polymer systems (among other things, structure, charge density, and molecular weight), the stoichiometric mixture ratio, the drug/polyelectrolyte ratio, the use of auxiliaries, such as low-molecular salt ions, and by further changes in the preparation protocol.

The advantages of the drug delivery system produced according to the invention compared to the known systems, such as liposomes or hollow capsules, are as follows:
  Size-scalability of the PEC particles from 10-1000 nm via polyelectrolyte and particle dimension and media parameters (concentration, pH, ionic strength);
  Adherability of the PEC/drug layers by adsorption (wet) or film formation (dry) while maintaining the form and function on the medical structure or material (therapy) or also on model substrates (screening, combinatorics);
  Adjustable binding or release potential of the drug by the type of interaction (electrostatic or physical inclusion), polymer structure or particle structure and size;
  Variability with regard to the drug.

The invention is explained in greater detail below relative to an exemplary embodiment.

Example 1

A bisphosphonate (pamidronate), an approved agent for osteoporosis therapy is used as a drug. The drug-loaded PEC dispersion was produced by mixing a 0.001M dextran sulfate solution (degree of substitution DS 3) with a 0.001M poly-L-lysine-(PLL) solution, which previously was mixed with a 0.01M bisphosphonate (BP) solution and a 0.01 m calcium chloride-($CaCl_2$) solution, both in molar ratios 4:1 (PLL/BP and PLL/$CaCl_2$) in a volume ratio 3:10. During the production of the non-stoichiometric mixtures of the dextran sulfate solution and the poly-L-lysine solution (polyanion and polycation) and of polyelectrolyte/drug, respectively, the excess component (poly-L-lysine) was respectively presented and the deficit component (dextran sulfate) was added.

50 microliter of this drug-loaded PEC dispersion was brushed onto an inorganic planar model substrate of germanium and dried in the drying oven at 50° C. The measurement of the release of the bisphosphonate and the stability of the PEC carrier layer was carried out via spectroscopic methods. After 24 hours a relative reduction of the bisphosphonate content of the PEC/drug layer of approximately 50% resulted. The PEC carrier layer remained stably bonded to the substrate after the release of the bisphosphonate. For a layer of the pure bisphosphonate applied and dried on the same model substrate as in the case of PEC/drug, after 1 minute an immediate detachment and thus a relative reduction of the bisphosphonate content of approximately 100% resulted.

The invention claimed is:

1. A method for producing a drug delivery system on the basis of polyelectrolyte complexes, comprising:
  producing a polyelectrolyte complex by one of:
    mixing polyelectrolytes comprising polyanions and polycations in a liquid in a non-stoichiometric ratio relative to charged monomer units, and adding at least one drug to the polyelectrolytes one of before, during and after the mixing; and
    mixing at least one charge-carrying drug and an oppositely charged polyelectrolyte, comprising polyanions or polycations in liquid; and
  applying a layer of the polyelectrolyte complex to a surface or a surface region of a medical structure or material, wherein a liquid component of the applied polyelectrolyte complex layer is removed by lowering the pressure.

2. The method according to claim 1, wherein the polyanions comprise at least one of anionic polypeptides, poly(L-glutamic acid), poly(D-glutamic acid), anionic polysaccharides, dextran sulfate, heparin, cellulose sulfate, carboxymethyl cellulose, carboxymethyl starch, alginate, carrageenan, xanthan, hyaluronic acid, and poly(acrylic acid).

3. The method according to claim 1, wherein the polycations comprise at least one of cationic polypeptides, poly(L-lysine), poly(D-lysine), cationic polysaccharides, diethylaminoethyl (DEAE) dextran, chitosan, cationic starch, poly(methylene-co-guanidine), and poly(ethyleneimine).

4. The method according to claim 1, wherein the liquid comprises water with adjusted pH value, ionic strength and temperature.

5. The method according to claim 1, wherein the producing the polyelectrolyte complex comprises the mixing the polyelectrolytes comprising the polyanions and the polycations in the liquid in the non-stoichiometric ratio relative to charged monomer units, and adding the at least one drug to the polyelectrolytes one of before, during and after the mixing,
wherein the polyanions and the polycations are mixed in a value coming as close as possible to the stoichiometric ratio of 1, relative to the charged monomer units.

6. The method according to claim 5, wherein the polyanions and the polycations are mixed in a non-stoichiometric ratio of (0.5 to <1) to (>1 to 2).

7. The method according to claim 6, wherein the polyanions and the polycations are mixed in a non-stoichiometric ratio of (0.9 to <1) to (>1 to 1.1).

8. The method according to claim 1, wherein the producing the polyelectrolyte complex comprises the mixing the polyelectrolytes comprising the polyanions and the polycations in the liquid in the non-stoichiometric ratio relative to charged monomer units, and adding the at least one drug to the polyelectrolytes one of before, during and after the mixing,
wherein the non-stoichiometric ratio of the polycations and polyanions is realized via utilizing different volumes with a same concentration of the polycations and the polyanions relative to the charged monomer units.

9. The method according to claim 1, wherein the producing the polyelectrolyte complex comprises the mixing the polyelectrolytes comprising the polyanions and the polycations in the liquid in the non-stoichiometric ratio relative to charged monomer units, and adding the at least one drug to the polyelectrolytes one of before, during and after the mixing,
wherein the polyanions are comprised in a polyanion solution and the polycations are comprised in a polycation solution, the method further comprising adding a charge-carrying drug to one of the polyanion solution and the polycation solution for the production of a drug-polyelectrolyte complex (PEC) dispersion.

10. The method according to claim 1, wherein the at least one drug is added in a quantity corresponding to a stoichiometric ratio to the charged monomer units of the oppositely charged polyelectrolyte of less than 1.

11. The method according to claim 1, wherein the at least one drug comprises a drug carrying single or multiple anionic and/or cationic charges, or charge-carrying antibiotics.

12. The method according to claim 11, wherein the at least one drug comprises bisphosphonates (BP).

13. The method according to claim 11, wherein the at least one drug comprises at least one of streptomycin, gentamicin, penicillin and nystatin.

14. The method according to claim 11, wherein the at least one drug comprises at least one of proton-pump inhibitors (PPI), statins (STA), and proteasome inhibitors (PSI).

15. The method according to claim 14, wherein the proton-pump inhibitors (PPI) comprise pantoprazole.

16. The method according to claim 14, wherein the statins comprise pravastatin.

17. The method according to claim 14, wherein the proteasome inhibitors (PSI) comprise bortezomib.

18. The method according to claim 1, wherein the at least one drug comprises at least one uncharged drug.

19. The method according to claim 1, wherein the at least one drug comprises a plurality of drugs, wherein the plurality of drugs are released in one of an identically and differently delayed manner.

20. The method according to claim 1, wherein the mixing of the polyelectrolytes comprises preparative process parameters.

21. The method according to claim 20, wherein the process parameters comprise at least one of order of addition, stirring rate, and consecutive steps of centrifuging-decanting-redispersing.

22. The method according to claim 1, wherein the producing the polyelectrolyte complex comprises the mixing the polyelectrolytes comprising the polyanions and the polycations in the liquid in the non-stoichiometric ratio relative to charged monomer units, and adding the at least one drug to the polyelectrolytes one of before, during and after the mixing,
wherein with the production of the non-stoichiometric mixtures of polyanion/polycation and of polyelectrolyte/drug, relative to the charged monomer units of the polyelectrolytes and the charged groups of the drug, a respective excess (or majority) component is presented, the method further comprising adding a respective deficit (or minority) component.

23. The method according to claim 1, wherein the producing the polyelectrolyte complex comprises producing a PEC dispersion, comprised chiefly of monomodally distributed nanoscale particles (polyelectrolyte complex (PEC) particles).

24. The method according to claim 1, wherein the producing the polyelectrolyte complex comprises producing polyelectrolyte complex (PEC) dispersions of polymodally distributed nanoscale particles with particle diameters in the range of 10 to 1000 nm.

25. The method according to claim 1, wherein the producing the polyelectrolyte complex comprises producing a polyelectrolyte complex (PEC) dispersion of PEC particles having at least one of soft and latex properties.

26. The method according to claim 1, wherein the applying the polyelectrolyte complex to the surface of the medical structure or material comprises one of adsorption, immersion, spraying, brushing, flowing over/streaming over, and the method further comprises drying the applied polyelectrolyte complex layer by raising the temperature, such that a solvent is removed, whereby a stable or irreversibly surface-bonded layer is produced.

27. The method according to claim 1, further comprising rinsing the applied polyelectrolyte complex layer with water after the applying the polyelectrolyte complex layer.

28. The method according to claim 1, wherein the medical structure or material comprises at least one of implants, bone-replacement materials, wound closures, and suture materials.

29. The method according to claim 1, wherein the positioning of the polyelectrolyte complex comprises a local injection.

30. The method according to claim 1, wherein the polyanions are comprised in a polyanion solution and the polycations are comprised in a polycation solution, the method further comprising adding at least one of inorganic salts and buffer substances to one of the polyanion solution and the polycation solution, to both the polyanion solution and the polycation solution, to the drug solution, to the polyelectrolyte/drug mixture, or to the polyelectrolyte complex (PEC) dispersion obtained by mixing.

31. The method according to claim 30, wherein the inorganic salt comprises calcium chloride.

32. The method according to claim 30, wherein the buffer substances comprises a citrate buffer.

* * * * *